(12) United States Patent
Peters et al.

(10) Patent No.: US 8,946,412 B2
(45) Date of Patent: Feb. 3, 2015

(54) DIAZABICYCLONONYL OXADIAZOLE COMPOUNDS AND THEIR USE AS NICOTINIC ACETYLCHOLINE RECEPTOR MODULATORS

(75) Inventors: Dan Peters, Malmo (SE); Daniel B. Timmermann, Herlev (DK); Elsebet Østergaard Nielsen, Copenhagen (DK); Tino Dyhring, Solrod (DK); Philip K. Ahring, Bagsvaerd (DK)

(73) Assignee: Danpet AB, Malmo (SE)

( * ) Notice: Subject to any disclaimer, the term of this patent is extended or adjusted under 35 U.S.C. 154(b) by 115 days.

(21) Appl. No.: 13/516,350

(22) PCT Filed: Dec. 16, 2010

(86) PCT No.: PCT/EP2010/069850
§ 371 (c)(1),
(2), (4) Date: Aug. 24, 2012

(87) PCT Pub. No.: WO2011/073296
PCT Pub. Date: Jun. 23, 2011

(65) Prior Publication Data
US 2013/0004428 A1    Jan. 3, 2013

Related U.S. Application Data

(60) Provisional application No. 61/289,794, filed on Dec. 23, 2009.

(30) Foreign Application Priority Data

Dec. 18, 2009   (DK) .................................. 2009 70283

(51) Int. Cl.
A61K 31/551   (2006.01)
A61K 51/04   (2006.01)
C07D 471/08   (2006.01)

(52) U.S. Cl.
CPC .......... C07D 471/08 (2013.01); A61K 51/0468 (2013.01)
USPC .............................. 540/556; 424/9.1; 424/9.4

(58) Field of Classification Search
USPC ........... 424/1.89, 9.1, 9.4; 514/221, 255, 364, 514/430; 540/556
See application file for complete search history.

(56) References Cited

U.S. PATENT DOCUMENTS

| | | |
|---|---|---|
| 2004/0266757 A1 | 12/2004 | Galli et al. |
| 2005/0020599 A1 | 1/2005 | Galli et al. |
| 2006/0122172 A1 | 6/2006 | Peters et al. |
| 2009/0118266 A1 | 5/2009 | Peters et al. |
| 2010/0216780 A1 | 8/2010 | Peters et al. |
| 2010/0280015 A1 | 11/2010 | Peters et al. |
| 2011/0105478 A1 | 5/2011 | Peters et al. |
| 2011/0112078 A1 | 5/2011 | Peters et al. |
| 2011/0208064 A1* | 8/2011 | Chongzhao et al. .......... 600/476 |
| 2011/0319397 A1 | 12/2011 | Peters et al. |
| 2012/0003153 A1 | 1/2012 | Peters et al. |
| 2012/0028968 A1 | 2/2012 | Peters et al. |

FOREIGN PATENT DOCUMENTS

| | | |
|---|---|---|
| WO | WO 2004/029053 A1 | 4/2004 |
| WO | WO2004029053 * | 4/2004 |
| WO | WO 2007/138037 A1 | 12/2007 |
| WO | WO 2007/138038 A1 | 12/2007 |
| WO | WO 2009/150138 A1 | 12/2009 |

OTHER PUBLICATIONS

Christer Halldin et al. (S)- and (R)-[11C] Nicotine and the Metabolite (R/S)-[11C] Cotinine. Preparation, Metabolite Studies and In Vivo Distribution in the Human Brain Using PET, Nucl. Med. Biol. vol. 19 (8), 871-880, 1992.*
International Search Report issued in PCT/EP2010/069850 dated May 4, 2011.
Muehllehner at al., "Positron emission tomography", Institute of Physics Publishing, Physics in Medicine and Biology, vol. 51, No. 13, Jul. 7, 2006, R117-R137.
Written Opinion of the International Searching Authority issued in PCT/EP2010/069850, dated May 24, 2011.

* cited by examiner

*Primary Examiner* — Michael G Hartley
*Assistant Examiner* — Jagadishwar Samala
(74) *Attorney, Agent, or Firm* — Birch, Stewart, Kolasch & Birch, LLP

(57) ABSTRACT

This invention relates to diazabicyclononyl oxadiazolyl derivatives, which are found to-be modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances. $Ar^1$ represents a pyrrolyl group, optionally substituted with alkyl or halo-alkyl.

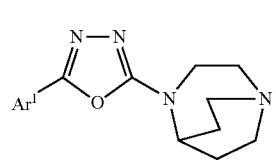

(I)

5 Claims, No Drawings

DIAZABICYCLONONYL OXADIAZOLE COMPOUNDS AND THEIR USE AS NICOTINIC ACETYLCHOLINE RECEPTOR MODULATORS

CROSS REFERENCE TO RELATED APPLICATIONS

This application is the National Phase of PCT/EP2010/069850 filed on Dec. 16, 2010, which claims priority under 35 U.S.C. §119(e) to U.S. Provisional Application No. 61/289,794 filed on Dec. 23, 2009 and under 35 U.S.C. §119(a) to Patent Application No. PA 2009 70283 filed in Denmark on Dec. 18, 2009, all of which are hereby expressly incorporated by reference into the present application.

TECHNICAL FIELD

This invention relates to diazabicyclononyl oxadiazolyl derivatives, which are found to be modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exerts its biological effect via two types of cholinergic receptors, the muscarinic Acetyl Choline Receptors (mAChR) and the nicotinic Acetyl Choline Receptors (nAChR).

Nicotinic acetylcholine receptors (nAChRs) are pentameric ligand gated ion channels and widely distributed throughout the central (CNS) and peripheral (PNS) nervous systems. At least 12 subunit proteins, i.e. α2-α10 and β2-β4, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition α4β2, while another major population of receptors is comprised of the homomeric α7.

Discovery of the important role played by nAChRs in several CNS disorders has called attention to these membrane proteins and to ligands able to modulate their functions. The existence of different subtypes at multiple levels has complicated the understanding of this receptor's physiological role, but at the same time has increased the efforts to discover selective compounds in order to improve the pharmacological characterization of this kind of receptor and to make safer the possible therapeutic use of its modulators.

WO 2004/029053, WO 2007/138037, WO 2007/138038 and WO 2009/150138 all describe oxadiazolyl-diazabicyclononane derivatives, which are found to be cholinergic ligands at the nicotinic acetylcholine receptors and modulators of the monoamine receptors and transporters. However, the labelled pyrrolyl-oxadiazole-diazabicyclononane derivatives of the present invention are not reported.

SUMMARY OF THE INVENTION

The present invention is devoted to the provision modulators of the nicotinic receptors, which modulators are useful for the treatment of diseases or disorders related to the nicotinic acetylcholine receptor (nAChR).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and abuse liability and withdrawal symptoms caused by the termination of abuse of chemical substances, in particular nicotine.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides a diazabicyclononyl oxadiazole derivative represented by Formula I

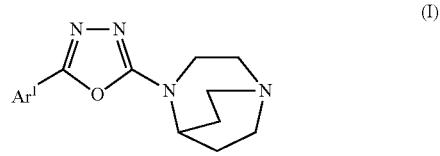

or a pharmaceutically acceptable salt thereof, in labelled or un-labelled form, wherein $Ar^1$ represents a pyrrolyl group, optionally substituted with alkyl or halo-alkyl.

In a second aspect the invention provides pharmaceutical compositions comprising a therapeutically effective amount of the diazabicyclononyl oxadiazole derivative of the invention, or a pharmaceutically acceptable salt thereof, together with at least one pharmaceutically acceptable carrier or diluent.

Viewed from another aspect the invention relates to the use of the diazabicyclononyl oxadiazole derivative of the invention, or a pharmaceutically acceptable salt thereof, for the manufacture of pharmaceutical compositions/medicaments for the treatment, prevention or alleviation of a disease or a disorder or a condition of a mammal, including a human, which disease, disorder or condition is responsive to modulation of cholinergic receptors.

In a further aspect the invention provides a method for treatment, prevention or alleviation of diseases, disorders or conditions of a living animal body, including a human, which disorder, disease or condition is responsive to modulation of cholinergic receptors, and which method comprises the step of administering to such a living animal body in need thereof a therapeutically effective amount of the diazabicyclononyl oxadiazole derivative of the invention.

In a further aspect the invention provides a method for the non-invasive determination of the distribution of a tracer compound inside a whole, intact living animal or human body using a physical detection method, wherein the tracer compound is a compound according to the invention, or a pharmaceutically acceptable salt thereof, in labelled form.

Other objects of the invention will be apparent to the person skilled in the art from the following detailed description and examples.

DETAILED DISCLOSURE OF THE INVENTION

Diazabicyclononyl Oxadiazole Derivatives

In its first aspect the invention provides a diazabicyclononyl oxadiazole derivative represented by Formula I

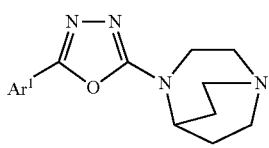

(I)

or a pharmaceutically acceptable salt thereof, in labelled or un-labelled form, wherein $Ar^1$ represents a pyrrolyl group, optionally substituted with alkyl or halo-alkyl.

In a preferred embodiment $Ar^1$ represents a pyrrolyl group, and in particular a 2-pyrrolyl group, optionally substituted with halo-alkyl.

In another preferred embodiment $Ar^1$ represents a pyrrolyl group, and in particular a 2-pyrrolyl group.

In a third preferred embodiment $Ar^1$ represents a pyrrolyl group, and in particular a 2-pyrrolyl group, substituted with halo-alkyl, and in particular 2-fluoroethyl.

In a fourth preferred embodiment $Ar^1$ represents a pyrrolyl group, and in particular a 2-pyrrolyl group, substituted with a labelled halo-alkyl, and in particular $^{18}F$-labelled 2-fluoroethyl.

In a fifth preferred embodiment $Ar^1$ represents a pyrrolyl group substituted with labelled halo-alkyl.

In a sixth preferred embodiment $Ar^1$ represents a pyrrolyl group substituted with $^{18}F$-labelled fluoro-alkyl.

In a seventh preferred embodiment the diazabicyclononyl oxadiazole derivative of the invention is a compound represented by Formula II

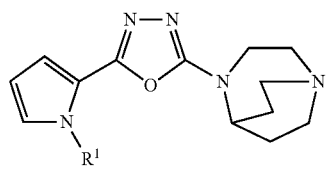

(II)

or a pharmaceutically acceptable salt thereof, in labelled or un-labelled form, wherein $R^1$ represents alkyl or halo-alkyl.

In an eight preferred embodiment the diazabicyclononyl oxadiazole derivative of the invention is a conpound represented by Formula II, in labelled form, wherein $R^1$ represents $[^{18}F]$-halo-alkyl.

In a tenth preferred embodiment the diazabicyclononyl oxadiazole derivative of the invention is
2-(1,4-Diazabicyclo[3.2.2]nonan-4-yl)-5-[1-(2-fluoroethyl) pyrrol-2-yl]-1,3,4-oxadiazole;
2-(1,4-Diazabicyclo[3.2.2]nonan-4-yl)-5-[1-(2-[$^{18}F$]fluoroethyl)pyrrol-2-yl]-1,3,4-oxadiazole; or
2-(1,4-Diazabicyclo[3.2.2]nonan-4-yl)-5-(1H-pyrrol-2-yl)-1,3,4-oxadiazole;
or a pharmaceutically acceptable salt thereof.

In an eleventh preferred embodiment the diazabicyclononyl oxadiazole derivative of the invention is
2-(1,4-Diazabicyclo[3.2.2]nonan-4-yl)-5-[1-(2-[$^{18}F$]fluoroethyl)pyrrol-2-yl]-1,3,4-oxadiazole;
or a pharmaceutically acceptable salt thereof.

Any combination of two or more of the embodiments described herein is considered within the scope of the present invention.

Labelled Compounds

In the context of this invention a labelled compound has one or more atoms replaced by an atom having an atomic mass or mass number different from the atomic mass or mass number usually found in nature. Such labelling will allow easy quantitative detection of the compound in question.

The labelled compounds of the invention may be useful as diagnostic tools, radio tracers, or monitoring agents in various diagnostic methods, and for in vivo receptor imaging, as described in more details below.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and iso-hexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention a haloalkyl group designates an alkyl group as defined herein, which alkyl group is substituted one or more times with halo. Preferred haloalkyl groups of the invention include 2-fluoroethyl.

Pharmaceutically Acceptable Salts

The diazabicyclononyl oxadiazole derivative of the invention may be provided in any form suitable for the intended administration. Suitable forms include pharmaceutically (i.e. physiologically) acceptable salts, and pre- or prodrug forms of the compound of the invention.

Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a compound of the invention include alkali metal salts, such as the sodium salt of a compound of the invention containing a carboxy group.

Methods of Producing Diazabicyclononyl Oxadiazole Derivatives

The diazabicyclononyl oxadiazole derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The labelled compounds according to the invention may be prepared as described in the art, e.g. by Deuther-Conrad et al. [Winnie Deuther-Conrad, Steffen Fischer, Achim Hiller, Elsebet østergaard Nielsen, Daniel Brunicardi Timmermann, Jörg Steinbach, Osama Sabri, Dan Peters and Peter Brust: Molecular imaging of α7 nicotinic acetylcholine receptors: design and evaluation of the potent radioligand [$^{18}$F] NS10743; *Eur. J. Nucl. Med. Mol. Imaging.* 2009 36 791-800], or as described in WO 96/39198.

Biological Activity

The present invention is devoted to the provision modulators of the nicotinic receptors, which modulators are useful for the treatment of diseases or disorders related to the nicotinic acetylcholine receptor (nAChR). Preferred compounds of the invention show affinity for binding to the $\alpha_7$-subtype of nicotinic acetylcholine receptors.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and abuse liability and withdrawal symptoms caused by the termination of abuse of chemical substances, in particular nicotine.

In a preferred embodiment the disease, disorder or condition relates to the central nervous system.

The compounds of the invention may also be useful as diagnostic tools or monitoring agents in various diagnostic methods, and in particular for in vivo receptor imaging (neuroimaging), and they may be used in labelled or unlabelled form.

In another preferred embodiment the disease, disorder or condition is a cognitive disorder, learning deficit, memory deficits and dysfunction, Down's syndrome, Alzheimer's disease, attention deficit, attention deficit hyperactivity disorder (ADHD), Tourette's syndrome, psychosis, depression, bipolar disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, amyotrophic lateral sclerosis (ALS), anxiety, non-OCD anxiety disorders, convulsive disorders, convulsions, epilepsy, neurodegenerative disorders, transient anoxia, induced neuro-degeneration, neuropathy, diabetic neuropathy, periferic dyslexia, tardive dyskinesia, hyperkinesia, pain, mild pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to postherpetic neuralgia, or to peripheral nerve injury, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Crohn's disease, inflammatory bowel disease, ulcerative colitis, diarrhoea, or abuse liability and withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the compounds of the invention are used for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to postherpetic neuralgia, or to peripheral nerve injury.

In another more preferred embodiment the compounds of the invention are used for the treatment, prevention or alleviation of smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a third more preferred embodiment the compounds of the invention are used for the treatment, prevention or alleviation of a neurodegenerative disorder, transient anoxia, or induced neuro-degeneration.

In a fourth more preferred embodiment the compounds of the invention are used for the treatment, prevention or alleviation of an inflammatory disorder, inflammatory skin disorder, acne, rosacea, Crohn's disease, inflammatory bowel disease, ulcerative colitis, or diarrhoea.

In a fifth more preferred embodiment the compounds of the invention are used for the treatment, prevention or alleviation of diabetic neuropathy, schizophrenia, cognitive or attentional deficits related to schizophrenia, or depression.

In a sixth more preferred embodiment the compounds of the invention are used for the treatment, prevention or alleviation of pain, in particular neuropathic pain, diabetic neuropathy, schizophrenia and cognitive or attentional deficits related to schizophrenia, depression, and for assisting in obtaining smoking cessation.

In a seventh more preferred embodiment the compounds of the invention are used the treatment of abuse liability and withdrawal symptoms caused by termination of use of addictive substances, in particular nicotine containing products such as tobacco, opioids such as heroin, cocaine and morphine, cannabis, benzodiazepines, benzodiazepine-like drugs, and alcohol.

In an eight more preferred embodiment the compounds of the invention are used for the treatment of anxiety, cognitive disorders, learning deficit, memory deficits and dysfunction, Down's syndrome, Alzheimer's disease, attention deficit, attention deficit hyperactivity disorder (ADHD), Parkinson's disease, Huntington's disease, Amyotrophic Lateral Sclerosis, Gilles de la Tourette's syndrome, psychosis, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, peripheral neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a ninth more preferred embodiment the compounds of the invention are used for the treatment of cognitive disorders, psychosis, schizophrenia and/or depression.

In a tenth more preferred embodiment the compounds of the invention are used for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In an eleventh more preferred embodiment the compounds of the invention are used for the treatment of endocrine disorders, such as thyrotoxicosis, pheochromocytoma, hypertension and arrhythmias.

In a twelfth more preferred embodiment the compounds of the invention are used for the treatment of neurodegenerative disorders, including transient anoxia and induced neuro-degeneration.

In a thirteenth more preferred embodiment the compounds of the invention are used for the treatment of inflammatory diseases, disorders, or conditions, including inflammatory skin disorders such as acne and rosacea, Crohn's disease, inflammatory bowel disease, ulcerative colitis, and diarrhoea.

In a fourteenth more preferred embodiment the compounds of the invention are used for the treatment of pain, mild, moderate or severe pain, or pain of acute, chronic or recurrent character, as well as pain caused by migraine, postoperative pain, and phantom limb pain. The pain may in particular be neuropathic pain, chronic headache, central pain, pain related to diabetic neuropathy, to postherpetic neuralgia, or to peripheral nerve injury.

Finally, in a most preferred embodiment, the compounds of the invention may be useful for the treatment of depression, cognition, dementia, obesity, or associated with abuse liability and withdrawal symptoms caused by nicotine addiction.

In this context "treatment" covers treatment, prevention, prophylactics and alleviation of abuse liability and withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Neuroimaging

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

The oxadiazolyl derivatives of the invention are useful as diagnostic tools or monitoring agents in various diagnostic methods, and in particular for in vivo receptor imaging (neuroimaging).

In another aspect of the invention, a method for the non-invasive determination of the distribution of a tracer compound inside a whole, intact living animal or human body using a physical detection method is provided. According to this method a tracer compound is a compound of the invention, or a pharmaceutically acceptable salt thereof, in labelled form.

In a preferred embodiment the physical detection method is selected from Positron Emission Tomography (PET), Single Photon Emission Computed Tomography (SPECT), Magnetic Resonance Spectroscopy (MRS), Magnetic Resonance Imaging (MRI), Computed Axial Tomography (CAT), Computed Tomography (CT), Functional Magnetic Resonance Imaging (fMRI), or combinations thereof.

The labelled compound of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{15}$O, $^{13}$N, $^{123}$I, $^{125}$I, $^{131}$I, $^{18}$F and $^{99m}$Tc.

Examples of commercially available labelling agents, which can be used in the preparation of the labelled compounds of the present invention are [$^{11}$C]O$_2$, $^{18}$F, and NaI with different isotopes of Iodine. In particular [$^{11}$C]O$_2$ may be converted to a [$^{11}$C]-methylating agent, such as [$^{11}$C]H$_3$I or [$^{11}$C]-methyl triflate.

The tracer compound can be selected in accordance with the detection method chosen.

In one preferred embodiment, the compounds of the invention labelled by incorporation of a isotope into the molecule, which may in particular be an isotope of the naturally occurring atoms including $^2$H (deuterium), $^3$H (tritium), $^{11}$C, $^{13}$C, $^{14}$C, $^{15}$O, $^{13}$N, $^{123}$I, $^{125}$I, $^{131}$I, $^{18}$F and $^{99m}$Tc, and the isotope incorporation may be measured by conventional scintillation counting techniques.

Labelled compounds of the invention may be prepared as described in the art, e.g. in WO 96/39198, or by Deuther-Conrad et al. [Winnie Deuther-Conrad, Steffen Fischer, Achim Hiller, Elsebet østergaard Nielsen, Daniel Brunicardi Timmermann, Jörg Steinbach, Osama Sabri, Dan Peters and Peter Brust: Molecular imaging of α7 nicotinic acetylcholine receptors: design and evaluation of the potent radioligand [$^{18}$F]NS10743; *Eur. J. Nucl. Med. Mol. Imaging.* 2009 36 791-800].

In another preferred embodiment, the physical method for detecting said tracer compound of the present invention is selected from Positron Emission Tomography (PET), Single Photon Emission Computed Tomography (SPECT), Magnetic Resonance Spectroscopy (MRS), Magnetic Resonance Imaging (MRI), Computed Axial Tomography (CAT), Computed Tomography (CT), Functional Magnetic Resonance Imaging (fMRI), or combinations thereof.

In a more preferred embodiment the compound of the invention is labelled by incorporation of $^{18}$F, and the isotope incorporation is measured by Positron Emission Tomography (PET) or Single Photon Emission Computed Tomography (SPECT).

In an even more preferred embodiment the compound of the invention is labelled by incorporation of $^{18}$F, and the isotope incorporation is measured by Positron Emission Tomography (PET).

Before conducting the method of the present invention, a diagnostically effective amount of a labelled compound of the invention is administered to a living body. The diagnostically effective amount of the labelled compound of the invention to be administered before conducting the in-vivo method for the present invention is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of a diazabicyclononyl oxadiazole derivative of the invention.

While a compound of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclononyl oxadiazole derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

In a preferred embodiment, when the pharmaceutical composition of the invention is intended for treating patients with abuse liability and withdrawal symptoms caused by nicotine addiction, formulations such as gums, patches, sprays, inhalers, aerosols, etc., are contemplated.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

The diazabicyclononyl oxadiazole derivatives of the present invention are valuable nicotinic acetylcholine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors, and which method comprises administering to such a living animal body, including a human, in need thereof an effective amount of a diazabicyclononyl oxadiazole derivative of the invention.

In the context of this invention the term "treatment" covers treatment, prevention, prophylaxis or alleviation, and the term "disease" covers illnesses, diseases, disorders and conditions related to the disease in question.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulfate was used as drying agent in the workup-procedures and solvents were evaporated under reduced pressure.

1,4-Diazabicyclo[3.2.2]nonane (Intermediate Compound)

The title compound was prepared according to J. Med. Chem. 1993 36 2311-2320 (and according to the slightly modified method described below).

1,4-Diazabicyclo[3.2.2]nonane (Intermediate Compound)

To the solution of 1,4-diazabicyclo[3.2.2]nonan-3-one (15.8 g; 113 mmol) in absolute dioxane (130 ml) LiAlH$_4$ (4.9 g; 130 mmol) was added under argon. The mixture was refluxed for 6 h and then allowed to reach room temperature. To the reaction mixture water (5 ml in 10 ml of dioxane) was added by drops, the mixture was stirred for 0.5 hour and then filtered off via glass filter. The solvent was evaporated and the residue was distilled using Kugelrohr apparatus at 90° C. (0.1 mbar) to yield 1,4-diazabicyclo[3.2.2]nonane (11.1 g; 78%) as colourless hygroscopic material.

1,4-Diazabicyclo[3.2.2]nonan-3-one (Intermediate Compound)

To the solution of 3-quinuclidinone hydrochloride (45 g; 278 mmol) in 90 ml of water hydroxylamine hydrochloride (21 g; 302 mmol) and sodium acetate (CH$_3$COONax3H$_2$O; 83 g; 610 mmol) were added, the mixture was stirred at 70° C. for 1 hour and then cooled to 0° C. The separated crystalline material was filtered off (without washing) and dried in vacuo to yield 40.0 g of oxime.

The 3-quinuclidinone oxime (40.0 g) was added during 2 hours by small portions to preheated to 120° C. polyphosphoric acid (190 g). The temperature of the solution during the reaction was kept at 130° C. After addition of all oxime the solution was stirred for 20 minutes at the same temperature, and was allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp. 211-212° C.

2-(1,4-Diazabicyclo[3.2.2]nonan-4-yl)-5-[1-(2-fluoroethyl)pyrrol-2-yl]-1,3,4-oxadiazole fumaric acid salt (Compound 1)

Was prepared according to method A-B-C from 5-[1-(2-fluoroethyl)pyrrol-2-yl]-1,3,4-oxadiazole-2-thiol (method A), 1-(2-fluoroethyl)pyrrole-2-carbohydrazide (method B) and methyl 1-(2-fluoroethyl)pyrrole-2-carboxylate (method C). LC-ESI-HRMS of [M+H]+ shows 306.17242 Da. Calc. 306.172468 Da, dev. −0.2 ppm.

Methyl 1-(2-fluoroethyl)pyrrole-2-carboxylate (Intermediate Compound)

Methyl 1H-pyrrole-2-carboxylate (3.0 g, 23.3 mmol) was solved in DMF (40 ml). Sodium hydride (1.40 g, 34.9 mmol, 60% in oil) was added and the mixture was stirred for 30 minutes at room-temperature. 1-Fluoro-2-iodoethane (4.1 g, 23.2 mmol) was added and the mixture was stirred for 15 h at 50° C. Water was added and the mixture was extracted with diethylether. The mixture was washed with saturated aqueous ammonium chloride. The product was purified chromatographically, using a mixture of petroleum and ethylacetate as eluent. Yield 1.1 g (28%).

2-(1,4-Diazabicyclo[3.2.2]nonan-4-yl)-5-[1-(2-[$^{18}$F]fluoroethyl)pyrrol-2-yl]-1,3,4-oxadiazole (Compound 2)

Prepared from 2-(1,4-diazabicyclo[3.2.2]nonan-4-yl)-5-(1H-pyrrol-2-yl)-1,3,4-oxadiazole free base and 1-[$^{18}$F]fluoro-2-iodoethane according to the conditions described above for methyl 1-(2-fluoroethyl)pyrrole-2-carboxylate.

Method A

2-(1,4-Diazabicyclo[3.2.2]nonan-4-yl)-5-(1H-pyrrol-2-yl)-1,3,4-oxadiazole free base (Compound 3)

A mixture of 1,4-diazabicyclo[3.2.2]nonane (3.02 g, 23.9 mmol), 5-(1H-pyrrol-2-yl)-1,3,4-oxadiazole-2-thiol (5.0 g, 20.9 mmol) and 1-pentanol (50 ml) was stirred for 15 h. The mixture was solved in chloroform and was filtered through celite. The mixture was purified three times by silica gel chromatography, using chloroform, methanol and aqueous ammonia (89:10:1). The product was dried and evaporated. Yield 382 mg (6%). LC-ESI-HRMS of [M+H]+ shows 260.15096 Da. Calc. 260.15059 Da, dev. 1.4 ppm.

Method B

5-(1H-Pyrrol-2-yl)-1,3,4-oxadiazole-2-thiol (Intermediate Compound)

Potassium hydroxide (4.78 g, 85.3 mmol) was solved in methanol (125 ml). 1H-pyrrole-2-carbohydrazide (9.7 g, 77.5 mmol) was added and the mixture was stirred for 30 minutes. Carbon disulfide (14.7 g, 193.8 mmol) was added to the mixture followed by stirring at 65° C. for 15 h. Another equivalent of carbon disulfide (5.90 g, 77.5 mmol) was added followed by stirring at 65° C. for 4 days. Aqueous hydrochloric acid (1 M) was added in excess quantity, the mixture was stirred and filtered and washed with aqueous hydrochloric acid. Yield 10 g (77%).

Method C

1H-Pyrrole-2-carbohydrazide (Intermediate Compound)

Hydrazine monohydrate (31.0 g, 620 mmol) was added to a mixture of methyl 1H-pyrrole-2-carboxylate (10 g, 77.5 mmol) and methanol (100 ml) followed by stirring at 65° C. for 15 h. The mixture was evaporated and the product was isolated as a crystalline solid.

Example 2

In vitro Inhibition of $^3$H-α-Bungarotoxine Binding in Rat Brain

In this example the affinity of a benzodioxolyl-oxadiazolyl-diazabicyclononane derivative of the invention for binding to a$_7$-subtype of nicotinic receptors is determined in a standard assay carried out essentially as described in e.g. WO 2006/087306.

The test value is presented as an IC$_{50}$ (the concentration of the test substance which inhibits the specific binding of $^3$H-α-bungarotoxin by 50%).

The result of this experiment is presented in Table 1 below.

TABLE 1

| Inhibition of $^3$H-α-Bungarotoxine Binding | |
|---|---|
| Compound No. | IC$_{50}$ (μM) |
| 1 | 0.011 |
| 3 | 0.017 |

The invention claimed is:

1. A diazabicyclononyl oxadiazole derivative represented by Formula I

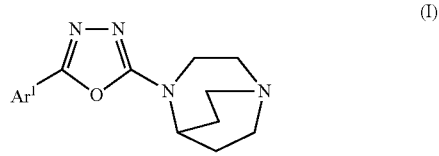

or a pharmaceutically acceptable salt thereof, in labelled or un-labelled form, wherein Ar$^1$ represents a pyrrolyl group substituted with labelled halo-alkyl.

2. The diazabicyclononyl oxadiazole derivative of claim 1, or a pharmaceutically acceptable salt thereof, wherein Ar$^1$ represents a pyrrolyl group substituted with $^{18}$F-labelled fluoro-alkyl.

3. The diazabicyclononyl oxadiazole derivative of claim 1, which is
   2-(1,4-Diazabicyclo[3.2.2]nonan-4-yl)-5-[1-(2-fluoroethyl)pyrrol-2-yl]-1,3,4-oxadiazole; or
   2-(1,4-Diazabicyclo[3.2.2]nonan-4-yl)-5-[1-(2-[$^{18}$F]fluoroethyl)pyrrol-2-yl]-1,3,4-oxadiazole;
   or a pharmaceutically acceptable salt thereof.

4. The diazabicyclononyl oxadiazole derivative of claim 1, which is
   2-(1,4-Diazabicyclo[3.2.2]nonan-4-yl)-5-[1-(2-[$^{18}$F]fluoroethyl)pyrrol-2-yl]-1,3,4-oxadiazole;
   or a pharmaceutically acceptable salt thereof.

5. A pharmaceutical composition comprising a therapeutically effective amount of a diazabicyclononyl oxadiazole derivative of any one of claims 1-4, or a pharmaceutically acceptable salt thereof together with at least one pharmaceutically acceptable carrier or diluent.

* * * * *